United States Patent [19]

Helder et al.

[11] 4,108,555
[45] Aug. 22, 1978

[54] TWO-BEAM COLORIMETER

[75] Inventors: Johan Helder, Brugge; Hubert De Steur, Drongen, both of Belgium; Wolfgang Pernegger, Erlangen, Fed. Rep. of Germany

[73] Assignee: Siemens Aktiengesellschaft, Berlin & Munich, Fed. Rep. of Germany

[21] Appl. No.: 674,050

[22] Filed: Apr. 5, 1976

[30] Foreign Application Priority Data

Apr. 28, 1975 [DE] Fed. Rep. of Germany ....... 2518857

[51] Int. Cl.² ............................................. G01J 3/48
[52] U.S. Cl. ................................................. 356/184
[58] Field of Search ...................... 315/71; 356/51, 39, 356/40, 173, 179, 180, 181, 184, 185, 186, 188, 189, 195, 201, 204–206; 250/226

[56] References Cited

U.S. PATENT DOCUMENTS

| 2,339,053 | 1/1944 | Coleman | 250/226 X |
| 3,010,798 | 11/1961 | Whitehead et al. | 356/181 X |
| 3,818,263 | 6/1974 | Belko | 315/71 X |

OTHER PUBLICATIONS

Shurkus, "Colorimetry", *Radio News,* Jun. 1944, pp. 25–27, 56, 58, 60 and 71.

*Primary Examiner*—F. L. Evans
*Attorney, Agent, or Firm*—Hill, Gross, Simpson, Van Santen, Steadman, Chiara & Simpson

[57] ABSTRACT

A two-beam colorimeter comprising an incandescent lamp, a resistor connected electrically in series with the incandescent lamp, a condenser and an interference filter disposed in side by side relation adjacent said incandescent lamp, a two-hole diaphragm for developing a comparison light beam and a measuring light beam, a reference filter disposed in the path of the comparison light beam, and an adjusting filter movable into and out of the path of the measuring light beam.

5 Claims, 1 Drawing Figure

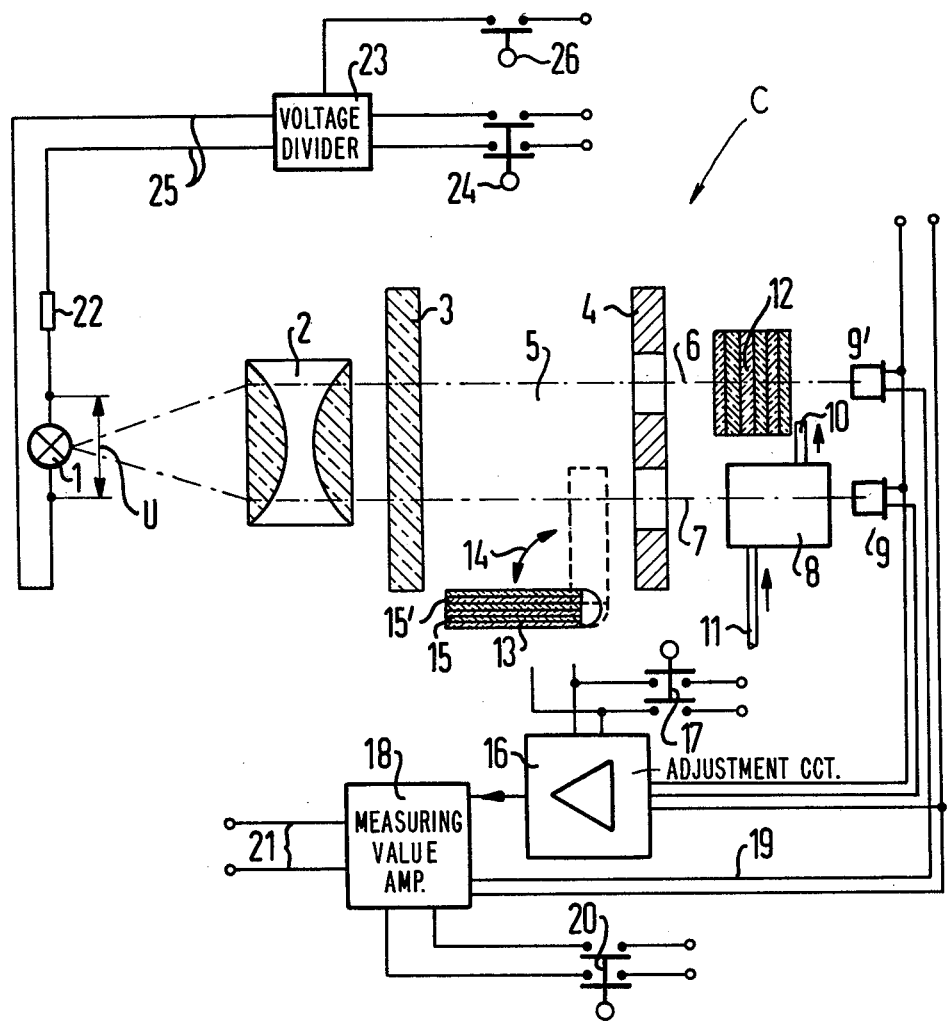

TWO-BEAM COLORIMETER

BACKGROUND OF THE INVENTION

This invention relates generally to the field of colorimetry and more particularly to an improved two-beam colorimeter.

Two-beam colorimeters are used for the colorimetric determination of a liquid component. They include an interference filter, the function of which is to filter only a specific band width out of a wide-band light produced by a light source. Also included is a reference filter, arranged in the path of a comparison beam, the function of which is, on the one hand, to compensate for the light absorption brought about by the measuring cuvette or vessel in which the sample or object liquid is contained, and on the other hand, to bring the photo-resistors, which may differ in their characteristics, to a common measurement level.

It has been determined that the reference filter, by itself, is not adequate to produce precise colorimetric measurement. For example, the cuvette is generally supplied by liquid by means of suitable conduits which interconnect the cuvette with another liquid container. Vapors can pass through the conduits into the cuvette, thereby causing the cuvette windows or the entire vessel to easily become cloudy. This, of course, can result in a mismeasurement.

A further shortcoming of known two-beam colorimeters lies in the fact that when the colorimeter is in continuous operation, the intensity of the light source diminishes, e.g., due to the vaporization of the filament. It is known that this deficiency can be alleviated by regulating the operating voltage of the light source, but circuitry suitable for this purpose is relatively expensive.

To provide a two-beam colorimeter which can operate relatively service-free as a module for an automatic analysis device, and which constantly produces accurate measurement values, and to otherwise improve upon and further develop two-beam colorimeters are objects of the present invention.

SUMMARY OF THE INVENTION

In accordance with the principles of the present invention, and to avoid the difficulties attendant vaporization within the cuvette, an adjusting filter is arranged for movement into and out of the path of the measuring beam before that beam encounters the cuvette. In addition, to avoid the difficulties attendant the reduction in intensity of the light source, a resistor is electrically connected in series therewith. This resistor possesses the same or substantially the same resistance as the light source (incandescent lamp).

In accordance with the invention, and prior to each colorimetric measurement, the measurement values of the two photo resistors, namely, the measuring beam photo resistor and the comparison beam photo resistor, are adjusted. During this adjustment the adjusting filter is moved into the path of the measuring beam. The colorimeter control device is then switched to an "adjustment" position, where the adjustment value is adjusted to agree with a given theoretical value. This adjustment is accomplished, as will be understood by those skilled in the art, in a known manner by means of a regulatable, automatically operating potentiometer.

Following the adjustment, the adjusting filter is moved out of the path of the measuring beam. The cuvette is then filled with the sample or object liquid, and following a period of quiescence, the colorimetric measurement is carried out.

In colorimeters of the type described herein above typically an incandescent lamp is used as the light source. It is generally known that such lamps must be operated with a constant voltage; no fluctuations in voltage in the power supply can be tolerated.

On the other hand, the wear of the filament of such lamps, and the attendant increase in internal resistance, cannot be avoided. When the internal resistance of the lamp increases, the current through the lamp decreases.

In accordance with the present invention a resistor is connected ahead of the lamp in the electric circuitry which contains the lamp. The voltage in the circuitry is increased such that the lamp itself retains its full operating voltage. By this arrangement, and in the event of a reduction in the current flow I through the lamp (as a consequence of filament wear), the voltage U, measured at the terminals of the lamp, increases, while the product $U \times I$ remains constant.

Thus with an increase in the filament resistance there occurs an increase in the voltage across the incandescent lamp, so that the light intensity thereof to a large extent remains constant.

Of course, with increased use of the lamp the increasing vaporization of the filament causes clouding of the lamp bulb, which also reduces light intensity. For approximately the first quarter of the useful life of the lamp, however, this clouding is slight in comparison to the drop in light yield caused by the wear of the filament. Hence the addition of a simple resistor in the lamp circuitry of a colorimeter provides a comparatively good stabilization of the light yield over a relatively long period of time.

Additional details and features of the present invention, along with other objects and advantages thereof, will be readily apparent from the following description of the preferred embodiment, taken in conjunction with the accompanying drawing, although variations and modifications may be effected without departing from the spirit and scope of the novel concepts disclosed herein.

BRIEF DESCRIPTION OF THE DRAWING

The drawing illustrates in a schematic and diagrammatic manner a colorimeter constructed and arranged in accordance with the principles of the present invention.

DESCRIPTION OF THE PREFERRED EMBODIMENT

Referring to the drawing, a colorimeter embodying the principles of the present invention is indicated generally at reference character C. Included therein is an incandescent lamp 1, whose light is transmitted (partially from a reflector, not shown) to a condenser 2, disposed adjacent the lamp 1, and thence to an interference filter 3, arranged in side by side relation with the condenser 2. The filter 3 is permeable only to light of a specific wave length, as will be understood by those skilled in the art.

A two-hole diaphragm 4 lies in the path of the light beam 5 which passes through the interference filter 3, thereby forming two beam paths, namely, a comparison beam 6 and a measuring beam 7. In the path of the measuring beam 7 is a measuring cuvette 8 in which the sample liquid is contained and behind which a photosensitive element 9 is located which receives the measuring beam after it is passed through the cuvette or vessel 8 and the contents thereof.

The measuring cuvette 8 is supplied with sample liquid through a conduit 11 connected to a suitable tank. Another conduit 10 is connected at one end to the cuvette 8 and at an opposite end to a syringe or the like suction producing device (not shown). Thus during the suction stroke of the syringe a vacuum condition is produced in the cuvette 8 and liquid is drawn thereinto through the conduit 11. After the sample liquid has been subjected to the colorimeter testing, the syringe is operated through a power stroke for forcing the sample liquid out of the cuvette 8 through the conduit 11.

Arranged in the path of the comparison beam 6 is a reference filter 12, the function of which is to maintain the light intensity of the comparison beam 6 at the same level as that of the measuring beam 7, after the measuring cuvette 8 has been emptied and with the adjusting filter 13 is pivoted into the path of the measuring beam 7.

It is generally known that it is not possible to keep the measuring cuvette 8 entirely free of impurities. A slight coating on the cuvette windows in the region through which the measuring beam 7 passes leads to mismeasurements.

In the present invention, these mismeasurements are avoided by means of the utilization of an adjusting filter 13 located between the interference filter 3 and the two-hole diaphragm 4. The adjusting filter 13 is pivotally mounted for movement into and out of the path of the measuring beam 7, as indicated by the double arrow at reference numeral 14.

Prior to each measurement, the adjusting filter 13 is pivoted into the path of the measuring beam 7, the adjusting filter 13 corresponding to the normal adsorption of the reduction in the light intensity which is brought about the the object liquid. The filter 13, therefore, comprises a plurality of individual filter plates 15, 15', etc., and can be matched to the object liquid by means of the selection of the individual filters.

When the adjusting filter 13 is pivoted into the path of the measuring beam 7, an automatic adjustment takes place prior to each measurement by means of an adjusting element 16, which is known to those having ordinary skill in the art. The pivoting of the adjusting filter 13 into the light path of the measuring beam 7 and the switching on of the adjusting element 16 is usually effected under the control of the programmer, by the closing of a switch 17. After the adjustment has been effected and the adjusting filter 13 has been pivoted out of the path of the measuring beam 7, the switch 17 is open (as shown) and the colorimeter C is now ready for operation.

In the measuring process, the measuring signal, which has been corrected by the adjusting element 16, passes to a measuring value amplifier 18. The comparison signal which has been established by a photosensitive element 9' is also connected, by means of a conductor 19, to the measuring value amplifier 18. A measurement or control value is present at the terminals 21 of the amplifier 18.

In accordance with the principles of the present invention, a resistor 22 is located in the electrical circuitry, indicated generally at reference numeral 25, ahead of the incandescent lamp 1. The circuit 25 is energized by the programmer by closing a series switch 24.

After the incandescent lamp 1 has been operated for a period of time the cross-section of the filament thereof decreases as a consequence of vaporization. As the filament decreases in cross-section the resistance thereof increases, so that the current consumption and thus the light yield decrease accordingly. With the series resistor 22 connected in series with the incandescent lamp 1 a voltage divider is obtained.

Thus, in the electric circuit 25 the voltage across the terminals thereof is arranged such that the terminal voltage U of the incandescent lamp 1 corresponds to its operating voltage. If the resistance of the incandescent lamp 1 increases, as a consequence of vaporization, the terminal voltage U also tends to increase, with a corresponding and simultaneous reduction in the current flow I. Thus the power consumption ($U \times I$) of the incandescent lamp 1 and the light yield thereof remain constant. This constancy avoids mismeasurements due to the ageing of the incandescent lamp 1, provided the operating duration or useful life of the incandescent lamp 1 is not overlooked.

In order to completely eliminate measuring errors which occur due to the clouding of the lamp bulb, it is suggested that the incandescent lamp 1 be changed after one quarter of its normal operating life, or at least no more than one-half of that life.

In order to prolong the operating life of the incandescent lamp 1, it is suggested that during the period between measurements the terminal voltage of the device which serves to maintain the voltage constant is not switched to "zero", but is instead maintained at a value approximately 25% below the normal operating voltage. By avoiding repeated heating and cooling of the incandescent lamp 1 it is possible to considerably increase the useful life thereof and, in a colorimeter, to ensure a uniform light-emission over a long period of time. This is, of course, a very critical feature so far as colorimeters are concerned.

To this end, the electric source or the like which serves to maintain the voltage constant includes an additional switch 26, which may be conveniently referred to as a measuring switch. Thus when the switches 24 and 26 are both closed, the incandescent lamp 1 is subjected to its full operating voltage.

Although minor modifications might be suggested by those versed in the art, it should be understood that we wish to embody within the scope of the patent warranted hereon all such modifications as reasonably come within the scope of our contribution to the art.

We claim as our invention:

1. A two-beam colorimeter comprising; in combination,
    a transparent cuvette for supporting an object liquid during an operational run and susceptible to residual impurities,
    first and second photo-sensitive photoelectric devices, said first photo-sensitive device disposed adjacent said cuvette,
    an incandescent light source, a condenser spaced from said light source and a diaphragm spaced from said condenser and including first and second apertures aligned with said first and second photo-sensitive devices to pass a measuring light beam and a reference light beam therethrough, respectively,
    a reference filter between said second aperture of said diaphragm and said second photo-sensitive device to compensate for the light absorption of said cuvette per se and differences in the operating characteristics of said first and second photo sensitive devices, selective adjusting filter means movable into said measuring light beam prior to an operational run on the object liquid to compensate for the natural light absorption of the object liquid in said cuvette and movable out of said measuring light beam during an operational run, said selective filter means being selectable in filtering characteristics to match the object liquid, an adjusting circuit connected to said first photo-sensitive device and operable in a first mode prior to an operational run to set to an attenuation factor representing the object liquid in said cuvette and operable in a second mode during an operational run to correspondingly factor the output of said first photo-sensitive device, and comparison means connected to said second photo-sensitive device and to said adjusting circuit to provide an signal during an operational run representing the colorimetric character of the object liquid.

2. The invention as defined in claim 1, wherein said adjusting filter comprises a plurality of selectable filter plates.

3. The invention as defined in claim 1, and including pivot means mounting said adjusting filter and enabling the same to be pivoted into and out of the path of said measuring light beam.

4. The invention as defined in claim 1, comprising a resistor connected in series with said light source and possessing substantially the same resistance as said light source.

5. The invention as defined in claim 1, comprising a series switch and a measuring switch arranged such that the light source is connected only to a partial voltage when said series switch is closed prior to an operational run and to the full nominal operating voltage when said measuring switch is closed during an operational run.

* * * * *